United States Patent [19]

Naumann et al.

[11] 4,021,221

[45] May 3, 1977

[54] PLANT-GROWTH-REGULATING COMPOSITIONS CONTAINING PHOSPHOLANIUM SALTS

[75] Inventors: Klaus Naumann, Cologne; Klaus Lürssen, Grosskoenigsdorf; Klaus Sasse, Schildgen, all of Germany

[73] Assignee: Bayer Aktiengesellschaft, Leverkusen, Germany

[22] Filed: May 28, 1975

[21] Appl. No.: 581,527

[30] Foreign Application Priority Data

June 14, 1974 Germany .......................... 2428672
May 7, 1975 Germany .......................... 2520315

[52] U.S. Cl. .................................. 71/86; 71/87
[51] Int. Cl.² .................................. A01N 9/36
[58] Field of Search .................... 71/86, 87

[56] References Cited

UNITED STATES PATENTS 3,142,685  7/1964  Buckler ...................... 71/87 X
3,531,514  9/1970  Redmore ..................... 71/86 X

OTHER PUBLICATIONS

Marsi, J.A.C.S., 91, 1969, pp. 4724–4729.
Issleib, et al., Ber., 94, 1961, pp. 113–117.
Cuddy, et al., 1971, Tetrahedron Letters, pp. 2397–2400.

Aksnes, et al., 19, 1965, Acta. Chem. Scand, pp. 931–934.

*Primary Examiner*—Joseph Paul Brust
*Attorney, Agent, or Firm*—Burgess, Dinklage & Sprung

[57] ABSTRACT

Compositions for regulating the growth of plants containing phospholanium salts of the formula:

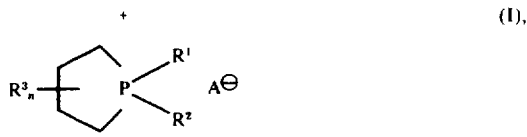

in which
R¹ is optionally substituted alkyl, alkenyl, alkynyl or cycloalkyl, or aralkyl which is optionally substituted in the aryl part,
R² is optionally substituted alkyl, alkenyl, alkynl or cycloalkyl, or aralkyl which is optionally substituted in the aryl part,
R³ is halogen or alkyl,
n is 0, 1 or 2, and
A⁻ is one equivalent of an anion of a nonphytotoxic acid are outstandingly useful to inhibit, enhance, or modify the growth of plants, even at relatively low dosages.

25 Claims, No Drawings

PLANT-GROWTH-REGULATING COMPOSITIONS CONTAINING PHOSPHOLANIUM SALTS

The present invention relates to plant growth regulating compositions containing certain phospholanium salts.

It is known that certain 2-haloethyl-trialkylammonium halides exhibit plant-growth-regulating properties from U.S. Pat. No. 3,156,554. Thus, for example, (2-chloroethyl)-trimethylammonium chloride can be used to influence plant growth, in particular to inhibit vegetative plant growth in cereals and other crop plants. However, the action of this compound is not always entirely satisfactory, especially if low amounts and low concentrations are used.

Surprisingly, the phospholanium salts used according to the present invention show a substantially greater plant-growth-regulating action than (2-chloroethyl)-trimethylammonium chloride, known from the state of the art, which is recognized to be a very effective compound of the same type of action. The compounds which can be used according to the present invention thus represent a valuable enrichment of the art.

The phospholanium salts used in this invention are of the formula

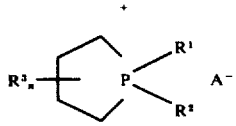
(I), in which
R$^1$ is optionally substituted alkyl, alkenyl, alkynyl or cycloalkyl, or aralkyl which is optionally substituted in the aryl part,
R$^2$ is optionally substituted alkyl, alkenyl, alkynl or cycloalkyl, or aralkyl which is optionally substituted in the aryl part,
R$^3$ is halogen or alkyl,
$n$ is 0, 1 or 2, and
A$^-$ is one equivalent of an anion of a nonphytotoxic acid.

The present invention thus provides a plant-growth-regulating composition containing as active ingredient, a compound of the formula (I), in admixture with a solid or liquefied gaseous diluent or carrier or in admixture with a liquid diluent or carrier containing a surface-active agent.

The present invention also provides a method of regulating the growth of plants which comprises applying to the plants or to a plant habitat a compound of the formula (I) alone or in the form of a composition containing as active ingredient a compound of the formula (I) in admixture with a diluent or carrier. The present invention further provides means of yielding plants the growth of which has been regulated by their being grown in areas in which immediately prior to and/or during the time of the growing a compound of the formula (I) was applied alone or in admixture with a diluent or carrier.

Preferably, in the formula (I), R$^1$ is straight-chain or branched alkyl of 1 to 4 carbon atoms (which alkyl radical can carry one or more substituents selected independently from hydroxyl, methoxy, methylcarbonyl, alkoxycarbonyl with 1 to 4 carbon in the alkoxy group, and halogen especially chlorine and bromine), alkenyl with 2 to 4 carbon atoms, cycloalkyl with 3 to 12 carbon atoms, especially with 3 to 7 carbon atoms, or aralkyl with 1 to 4 carbon atoms in the alkyl part and 6 to 10 carbon atoms in the aryl part, which aryl part may be optionally substituted by halogen, for example chlorine, R$^2$ is straight-chain or branched alkyl with 1 to 4 carbon atoms (which alkyl radical can carry one or more substituents selected independently from hydroxyl, methoxy, methylcarbonyl, alkoxycarbonyl with 1 to 4 carbon atoms in the alkoxy group, and halogen, especially chlorine and bromine), alkenyl with 2 to 4 carbons atoms, alkynyl with 2 to 4 carbon atoms, cycloalkyl with 3 to 12 carbon atoms, especially with 3 to 7 carbon atoms, or aralkyl with 2 to 4 carbon atoms in the alkyl part and 6 to 10 carbon atoms in the aryl part, which aryl part may be optionally substituted by halogen, for example chlorine; R$^3$ is chlorine, bromine or straight-chain or branched alkyl with 1 to 4 carbon atoms; $n$ 0, 1 or 2; and A$^-$ is halide, especially chloride, bromide or iodide, tetrafluoroborate or alkyl-sulphate, especially methyl-sulphate or ethyl-sulphate.

The following may be mentioned as examples of the active compounds which can be used according to the invention: 1,1-dimethylphospholanium chloride, 1,1-dimethylphospholanium methosulphate, 1,1-diethyl-phospholanium bromide, 1-methyl-1-ethylphospholanium bromide, 1-methyl-1-benzylphospholanium chloride, 1-methyl-1-(2-hydroxyethyl)-phospholanium chloride, 1-methyl-1-(2-chloroethyl)-phospholanium chloride, 1-methyl-1-ethoxycarbonylmethyl-phospholanium chloride, 1,1,2-trimethylphospholanium chloride, 1,1,3-trimethyl-phospholanium chloride and 1,1-dimethyl-3,4-dichloro-phospholanium chloride.

Some of the compounds which can be used according to the invention are known (see J. Amer. Chem. Soc. 91, 4724–4729 (1969); Ber. 94, 113–117 (1961); Acta Chem. Scand. 19, 931–934 (1965); Tetrahedron Lett. 1971 2397–2400). However, their use as plant growth regulators is new.

Those compounds which can be used according to the invention and which have not yet been described in the literature can be prepared in a simple manner in accordance with known processes.

For example, the compounds are obtained when
a. a phospholane of the general formula

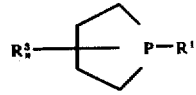
(II), in which
R$^1$, R$^3$ and $n$ have the above-mentioned meanings,
is reacted with a compound of the general formula

 (III)

in which
R$^4$ is optionally substituted alkyl, alkenyl, alkynyl or cycloalkyl, aralkyl which is optionally substituted in the aryl part, or a triethyloxonium ion, and
X is halogen, alkyl-sulphate or tetrafluoborate, optionally in the presence of a solvent, at temperatures between 0° and 130°, or b. a phospholanium salt, obtainable according to process (a), of the general formula

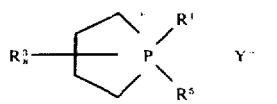

in which

R¹, R³ and n have the above-mentioned meanings,
R⁵ is alkyl substituted by a hydroxyl group and
Y is halide, alkyl-sulphate or tetrafluoborate,
is reacted, optionally in the presence of a solvent, such as chloroform, and optionally in the presence of a catalyst, such as dimethylformamide, with a halogenating agent, such as thionyl chloride, at temperatures between 0° and 130° C, or c. a phospholenium salt of the general formula

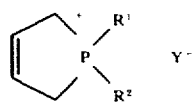

in which

R¹, R² and y have the above-mentioned meanings,
is reacted, optionally in the presence of a solvent, such as, chloroform, with a halogenating agent, such as chlorine, at temperatures between 0° to 130° C.

The phospholanes of the formula (II) which are to be used as starting materials in carrying out process (a) are known or can be prepared in accordance with previously described processes (see J. Amer. Chem. Soc. 91, 4724–29 (1969)). The following may be mentioned as examples of phospholanes of the formula (II): 1-methyl-phospholane, 1-ethyl-phospholane, 1,3-dimethyl-phospholane, 1-n-hexyl-phospholane and 1-cyclohexyl-phospholane.

The compounds of the formula (III) which are also to be used as starting materials in carrying out process (a) are also known. The following may be mentioned as examples: methyl iodide, methyl chloride, ethyl bromide, propyl chloride, allyl chloride, propargyl chloride, benzyl chloride, chloroacetone, chloroacetetic acid or its esters, chloromethyl ether, chloromethyl-naphthalene, dimethyl sulphate, diethyl sulphate and triethyloxonium tetrafluoborate.

Preferred solvents which can be used in carrying out process (a) are lower alcohols, for example methanol, hydrocarbons, such as toluene and cyclohexane, and dimethylformamide, acetonitrile, acetone or water.

In carrying out process (a), preferably 1 mole of the starting compound of the formula (III) is employed per mole of the phospholane of the Formula (II). It is possible to use higher or lower ratios than the stated stoichiometric ratio but this produces no significant improvement in yield.

In preparing the compounds, usable in accordance with the invention, by process (a), the reaction products are either directly obtained in a crystalline form after completion of the reaction or can be separated out in an oily state by adding a solvent in which they are insoluble. The crystalline products are isolated by a simple filtration, if necessary after first concentrating the reaction mixture. Additional purification can be effected by reprecipitation. If the reaction products are obtained as oils, they are isolated by first separating the phases and then purifying the oil by treating it, in aqueous or alcoholic solution, with active charcoal.

In carrying out process (b), preferably 1.1 to 1.5 equivalents of halogenating agent, and a small amount of catalyst, are employed per mole of the phospholanium salt of the formula (IV). It is possible to use higher or lower ratios than the stoichiometric ratio but this produces no significant improvement in yield.

When employing process (b), the reaction products are isolated in accordance with customary methods. A suitable procedure is to concentrate the reaction mixture under reduced pressure after completion of the reaction, take up the residue which is left in a suitable solvent, purify the solution with active charcoal and then concentrate, under reduced pressure, the solution obtained after filtration.

The phospholenium salts of the formula (V) which can be used as starting materials in carrying out process (c) are known or can be prepared in accordance with previously described methods (see J. Chem. Soc. 1968, 929–931). The following may be mentioned as examples of phospholenium salts of the formula (V): 1,1-dimethyl-3-phospholenium chloride and 1,1-diethyl-3 phospholenium chloride.

In carrying out process (c), preferably 1 equivalent of a halogenating agent is employed per mole of phospholenium salt of the formula (V). It is possible to use higher or lower ratios than the stated stoichiometric ratio but this produces no significant improvement in yield.

When employing process (c), the reaction products are conveniently isolated by concentrating the reaction mixture after completion of the reaction, and filtering off the crystals which separate out. Additional purification can be achieved by reprecipitation. If the reaction products are obtained in the form of oils, they can be converted to the crystalline state by digestion with a polar solvent, such as acetone, and be obtained pure after filtration.

The preparation of the compounds of the formula (I) is illustrated by the following Examples.

EXAMPLE 1

Preparation of 1-methyl-1-ethoxy-carbonylmethyl-phospholanium bromide

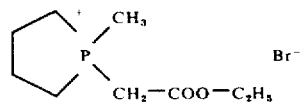

33.4 g (0.2 mole) of ethyl bromoacetate were added to a solution of 20.4 g (0.2 mole) of 1-methylphospholane in 200 ml of toluene at room temperature, whilst stirring. The reaction mixture was then left to stand for some hours at room temperature and the precipitate which had separated out was then filtered off. This gave 1-methyl-1-ethoxycarbonylmethyl-phospholanium bromide in the form of crystals which decomposed on heating at 122° C.

Analysis: ($C_9H_{18}O_2PBr$). Calculated: 29.8%, Br. Found: 29.1%, Br.

The infrared spectrum showed a strong carbonyl band.

EXAMPLE 2

Preparation of
1-methyl-1-(2-hydroxyethyl)-phospholanium chloride

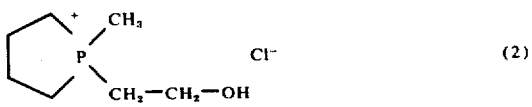

(2)

16.1 g (0.2 mole) of 2-chloroethanol were added to a solution of 20.4 g (0.2 mole) of 1-methyl-phospholane in 200 ml of toluene at room temperature, whilst stirring. The reaction mixture was then left to stand for some hours at room temperature and the precipitate which had separated out was then filtered off. This gave 1-methyl-1-(2-hydroxyethyl)-phospholanium chloride in the form of hygroscopic crystals of melting point 78°–80° C.

Example 3

Preparation of
1-methyl-1-(2-chloroethyl)-phospholanium chloride

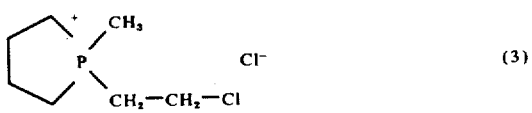

(3)

27.3 g (0.23 mole) of thionyl chloride were added dropwise, whilst stirring, to a solution of 36.5 g (0.2 mole) of 1-methyl-1(2-hydroxyethyl)-phospholanium chloride in 200 ml of chloroform and a small amount of dimethylformamide at 65° C. When the evolution of hydrogen chloride had subsided, the reaction mixture was concentrated under reduced pressure and the residue which remained was taken up in water. The solution thereby produced was treated with active charcoal and then filtered. Concentration of the filtrate under reduced pressure gave 1-methyl-2-(2-chloroethyl)-phospholanium chloride in the form of a crystal hydrate from which water was eliminated on warming at 70° C. The substance which remained melted above 250° C.

Analysis: ($C_7H_{15}PCl_2$). Calculated: 35.5%, Cl. Found: 36.0%, Cl.

EXAMPLE 4

Preparation of
3,4-dichloro-1,1-dimethyl-phospholanium chloride

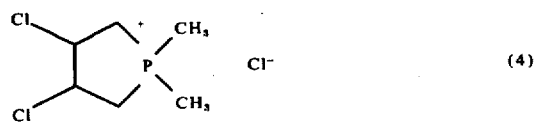

(4)

44.3 g (0.2 mole) of 1,1-dimethyl-3-phospholenium chloride were suspended in 250 ml of chloroform and reacted with 14.2 g (0.2 mole) of chlorine at 20° C. After completion of the reaction, the reaction mixture was concentrated under reduced pressure. This gave 3,4-dichloro-1,1-dimethyl-phospholanium chloride in the form of colourless crystals of melting point 90°–100° C (decomp.).

EXAMPLE 5

Preparation of 1,1-dimethylphospholanium chloride
and monohydrate

(5)

The known 1,1-dimethylphospholaniumbromide[J. Amer. Chem. Soc. 91, 4724 (1969)]was converted into the corresponding chloride by means of ion exchange resin charged with sodium chloride. The aqueous solution was evaporated in vacuo to give the monohydrate as a viscous oil.

Analysis: ($C_6H_{14}ClP·H_2O$). Calculated: 20.6%, Cl. Found: 20.0%, Cl.

EXAMPLE 6

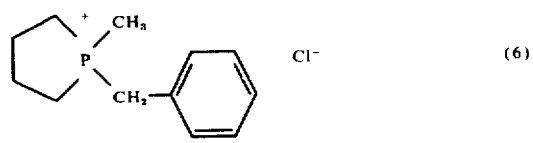

(6)

25,3 g (0,2 mole) of benzyl chloride were added to a solution of 20,4 g (0,2 mole) of 1-methylphospholane in 200 ml of toluene at room temperature, whilst stirring. The reaction mixture was then left to stand for some hours at room temperature and the precipitate which had separated out was then filtered off. This gave 1-methyl-1-benzyl-phospholanium chloride in the form of crystals which decomposed on heating.

Analysis: ($C_{12}H_{18}PCl$). Calculated: 63.0%, C; 7.9%, H; 13.0%, P. Found: 63.2%, C; 8.0%, H; 13.2%, P.

EXAMPLE 7

Preparation of 1,1-dimethylphospholanium
methosulfate

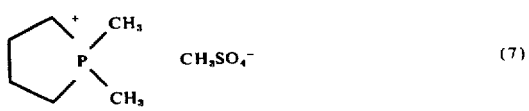

(7)

126 g. (1 mol) of dimethylsulfate were added to a solution of 102 g of 1-methylphospholane in 1 1 toluene at room temperature, whilst stirring. After 10 hours the crystalls which had separated were filtered off to give 1,1-dimethylphospholanium methosulfate. m.p. 126° C Analysis: ($C_7H_{17}O_4PS$) Calculated: 36.9%, C; 7.4%, H; 13.6%, P; 14.1%, S. Found: 36.6%, C; 7.2%, H; 12.9%, P; 14.6%, S.

The active compounds which can be used according to the invention affect the the metabolism of plants and can therefore be used as growth regulators.

With regard to the mode of action of plant growth regulators, previous experience has shown that an active compound can exert one or more different effects on plants. Effects of the compounds depend essentially on the point of time at which they are used, relative to the stage of development of the seed or of the plant, and on the amounts of active compound applied to the plants or their environment, and on the method of application. In each case, growth regulators should have a positive influence, of the desired type, on the crop plants.

Plant growth regulators can be used, for example, to inhibit vegetative plant growth. Such inhibition of growth is of economic interest, inter alia, in the case of grasses, since it is, for example, possible by repressing the growth of grass, to reduce the frequency of mowing in horticultural gardens, parks and sports fields or road verges. The inhibition of growth of herbacious and woody plants on road verges, and in the vicinity of transmission lines, or, quite generally, in areas where heavy plant growth is undesirable, is also of importance.

The use of growth regulators to inhibit the growth in length of cereals is also important, since a shortening of the stem reduces or completely eliminates the danger of lodging of the plants before harvesting. Furthermore, growth regulators can cause a strengthening of the stem in cereals, which also counteracts falling-over.

Inhibition of vegetative growth permits denser planting of the crop in the case of many crop plants, so that an improved yield per unit area of soil can be achieved.

A further mechanism of increasing the yield by means of growth inhibitors is based on the fact that the nutrients benefit blossoming and fruit formation to a greater extent, whilst vegetative growth is restricted.

Using growth regulators promotion of vegetative growth can also frequently be achieved. This is of great utility if it is the vegetative parts of the plants which are harvested. Promoting the vegetative growth can, however, also simultaneously lead to a promotion of generative growth so that, for example, more fruit, or larger fruit, is formed.

Increases in yield can in some cases also be achieved by affecting the plant metabolism without changes in vegetative growth becoming noticeable. Growth regulators can furthermore bring about a change in the composition of the plants, so as to result in better quality of the harvested products. Thus, for example, it is possible to increase the sugar content in sugar beet, sugar cane, pineapple and citrus fruit or to increase the protein content in soya or cereals.

Parthenocarpous fruit can be formed under the influence of growth regulators. Furthermore, the gender of the flowers can be influenced.

Using growth regulators it is also possible favorably to influence the product or efflux of secondary plant materials. The stimulation of latex flow in rubber trees may be mentioned as an example.

During the growth of the plant, the lateral branching can be increased, through the use of growth regulators, as a result of chemical breaking of the apical dominance. There is interest in this, for example, in the case of plant propagation by cuttings. However, it is also possible to inhibit the growth of side shoots, for example to prevent the formation of side shoots in tobacco plants after decapitation, and thus to promote leaf growth.

Under the influence of growth regulators, the amount of leaf on plants can be so controlled as to achieve defoliation of the plants at a desired point of time. Such defoliation is of interest to facilitate mechanical harvesting, for example in the case of grapes or cotton, or to lower the transpiration at a point in time at which the plant is to be transplanted.

Premature shedding of fruit can be prevented by use of growth regulators. However, it is also possible to assist the shedding of fruit — for example edible fruit — in the sense of a chemical thinning out, up to a certain degree. Growth regulators can also serve to reduce the force required to detach the fruit from crop plants at harvest time, so that mechanical harvesting of the plants is made possible or manual harvesting is facilitated.

Using growth regulators it is furthermore possible to accelerate or delay the ripening of the crop before or after harvesting. This is of particular advantage because as a result optimum adaptation to market requirements is achievable. Furthermore, growth regulators can in some cases improve the coloration of fruit. In addition, a reduction in time spread within which a ripe state is attained is also achievable with the aid of growth regulators. This provides the prerequisites for being able to carry out a complete mechanical or manual harvesting in one stage only, for example in the case of tobacco, tomatoes or coffee.

The latent period of seeds or buds of plants, that is to say the endogenic annual rhythm, can also be influenced by the use of growth regulators, so that the plants, such as, for example, pineapple or horticultural plants in nurseries germinate, shoot or blossom at a point in time at which they normally show no readiness to do so.

Using growth regulators it is also possible to delay the shooting of buds or the germination of seeds, for example to avoid damage by late frosts in regions where frost is a hazard.

Growth regulators can also make crop plants halophilic. This provides the prerequisites for being able to cultivate plants on soil containing salt.

Using growth regulators it is also possible to induce frost resistance and drought resistance in plants.

The active compounds according to the present invention can be converted into the usual formulations, such as solutions emulsions, suspensions, powders, pastes and granulates. These may be produced in known manner, for example by mixing the active compounds with extenders, that is, emulsifying agents and-/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaoline, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds to be used according to the invention can be present in the formulations as a mixture with other active compounds such as fungicides, insecticides, acaricides and herbicides, and as a mixture with fertilizers.

The formulations in general contain from 0.1 to 95 per cent by weight of active compound, preferably from 0.5 to 90 per cent by weight.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be applied in the usual manner, for example by watering, spraying, atomizing, scattering, dusting, foaming, gassing and the like. It is furthermore possible to apply the active compounds in accordance with the ultra-low-volume (ULV) method, to spread the active-compound preparation or the active compound itself on plants or parts of plants or to inject the active-compound preparation or the active compound itself into the soil. It is also possible to treat the seed of the plants.

The active-compound concentrations can be varied within a fairly wide range. In general, concentrations of 0.00005 to 2%, preferably of 0.0001 to 0.5%, by weight are used. Furthermore, 0.01 to 50 kg, preferably 0.05 to 10 kg, of active compound are generally used per hectare of soil area.

The preferred portion of time within which the growth regulators are employed depends on the climatic and vegetative circumstances.

The Examples which follow show the activity of the compounds according to the invention as growth regulators without excluding the possibility of other applications as growth regulators.

EXAMPLE A

Inhibition of growth/wheat

Solvent: 10 parts by weight of methanol
Emulsifier: 2 parts by weight of polyethylene sorbitan monolaurate To produce a suitable preparation of active compound, 1 part by weight of active compound was mixed with the stated amounts of solvent and emulsifier and made up to the desired concentration with water.

Young wheat plants in the two-leaf stage were sprayed with the preparation of active compound until dripping wet. After the untreated control plants had grown to a height of about 60 cm, the additional growth of all plants was measured and the inhibition in growth, in % of the additional growth of the control plants, was calculated. 100% denotes cessation of growth and 0% denotes a growth corresponding to that of the untreated control plants.

The active compounds, active compound concentrations and results can be seen from the table which follows:

Table A

| Active compound | Inhibition of growth/wheat | |
|---|---|---|
| | Concentration in % | Inhibition of growth in % of the control |
| Water (control) | — | 0 |
| Cl—CH$_2$—CH$_2$—N(CH$_3$)$_3$ Cl$^-$ (known) | 0.05 | 40 |
| (5) | 0.05 | 40 |
| (7) | 0,05 | 40 |

At the end of the experiment, the leaf color and thickness of stem was, in addition, assessed for all plants.

It was found that the plants treated with the active compounds according to the present invention showed a strong dark green leaf color, in contrast to the untreated control plants and to the plants treated with the comparison substance. Furthermore, the plants treated with the active compounds according to the present invention had markedly thicker stems than the untreated control plants and the plants treated with the comparison substance. It is particularly this observed strengthening of the stems which is of decisive importance in preventing lodging.

EXAMPLE B

Inhibition of growth/beans

Solvent: 10 parts by weight of methanol
Emulsifier: 2 parts by weight of polyethylene sorbitan monolaurate To produce a suitable preparation of active compound, 1 part by weight of active compound was mixed with the stated amounts of solvent and emulsifier and made up to the desired concentration with water.

Young bean plants, in the stage at which the primary leaves had fully unfolded, were sprayed with the preparations of active compound until dripping wet. After 2 weeks the additional growth was measured and the inhibition in growth was calculated in % of the additional growth of the control plants. 100% denotes cessation of growth and 0% denotes a growth corresponding to that of the untreated control plants.

The active compounds, active compound concentrations and results can be seen from the table which follows:

Table B

| Active compound | Inhibition of growth/beans | |
|---|---|---|
| | Concentration in % | Inhibition of growth in % of the control |
| Water (control) | — | 0 |

Table B-continued

Inhibition of growth/beans

| Active compound | Concentration in % | Inhibition of growth in % of the control |
|---|---|---|
| 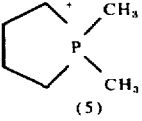 (5) | 0.05 | 20 |
| 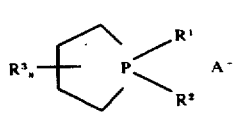 (6) | 0.05 | 40 |

It will be appreciated that the instant specification and examples are set forth by way of illustration and not limitation, and that various modifications and changes may be made without departing from the spirit and scope of the present invention.

What is claimed is:

1. Method of regulating growth of plants which method comprises applying to the plants or their habitat a growth regulating effective amount of plant-growth-regulating composition containing as active ingredient a phospholanium salt of the general formula:

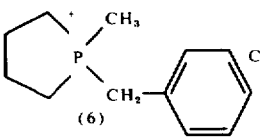

(I).

in which
R$^1$ is alkyl of 1 to 4 carbon atoms, substituted alkyl substituted with at least 1 of hydroxyl, methoxy, methylcarbonyl, alkoxy carbonyl of 1 to 4 carbon atoms in the alkoxy group and halogen, alkenyl or alkynyl of up to 4 carbon atoms, or cycloalkyl of 3 to 12 carbon atoms, aralkyl of 1 to 4 carbon atoms in the alkyl moiety and 6 to 10 carbon atoms in the aryl moiety, or substituted aralkyl wherein the aryl moiety is substituted with halogen;

R$^2$ is alkyl of up to 4 carbon atoms, substituted alkyl wherein the substituent is selected from hydroxyl methoxy, methylcarbonyl, alkoxy carbonyl of 1 to 4 carbon atoms in the alkoxy group and halogen; alkenyl or alkynyl of up to 4 carbon atoms, cycloalkyl of 3 to 12 carbon atoms, aralkyl of 2 to 4 carbon atoms in the in the alkyl moiety and 6 to 10 carbon atoms in the aryl moiety, substituted aralkyl wherein the aryl moiety is substituted with halogen, R$^3$ is halogen or alkyl of up to 4 carbon atoms, $n$ is 0, 1 or 2, and A$^-$ is one equivalent of an anion of a non-phytotoxic acid, in admixture with an argriculturally acceptable carrier.

2. Method as claimed in claim 1 wherein R$^1$ in the formula is alkyl of from 1 to 4 carbon atoms.

3. Method as claimed in claim 1 wherein R$^1$ is substituted alkyl of from 1 to 4 carbon atoms wherein the substituents are selected from hydroxyl, methoxy, methylcarbonyl, alkoxylcarbonyl of from 1 to 4 carbon atoms in the alkoxy group, and halogen.

4. Method as claimed in claim 1 wherein R$^1$ is alkenyl or alkynyl of up to 4 carbon atoms.

5. Method as claimed in claim 1 wherein R$^1$ is cycloalkyl of from 3 to 12 carbon atoms.

6. Method as claimed in claim 1 wherein R$^1$ is aralkyl or haloaralkyl.

7. Method as claimed in claim 1 wherein R$^2$ is alkyl or substituted alkyl of from 1 to 4 carbon atoms.

8. Method as claimed in claim 1 wherein R$^2$ is alkenyl or alkynyl of up to 4 carbon atoms.

9. Method as claimed in claim 1 wherein R$^2$ is cycloalkyl of from 3 to 12 carbon atoms.

10. Method as claimed in claim 1 wherein R$^2$ is aralkyl or haloaralkyl.

11. Method as claimed in claim 1 wherein R$^3$ is halogen.

12. Method as claimed in claim 1 wherein R$^3$ is alkyl of up to 4 carbon atoms.

13. Method as claimed in claim 1 wherein $n$ is 0.

14. Method as claimed in claim 1 wherein $n$ is 1 or 2.

15. Method as claimed in claim 1 wherein A$^-$ is selected from chloride, bromide, iodide, tetrafluoroborate or alkylsulphate.

16. Method as claimed in claim 1 wherein said phospholanium salt is 1-methyl-1-ethoxy-carbonylmethyl-phospholanium bromide.

17. Method as claimed in claim 1, wherein said phospholanium salt is 1-methyl-1-benzyl-phospholanium chloride.

18. Method as claimed in claim 1 wherein said phospholanium salt is 1-methyl-1(2-chloroethyl)-phospholanium chloride.

19. Method as claimed in claim 1 wherein said phospholanium salt is 3,4-dichloro-1,1-dimethyl-phospholanium chloride.

20. Method as claimed in claim 1 wherein said phospholanium salt is 1,1-dimethylphospholanium chloride.

21. Method as claimed in claim 1 wherein said phospholanium salt is 1,1-dimethylphospholanium methosulfate.

22. Method as claimed in claim 1 wherein said phospholanium salt is selected from the group consisting of 1-methyl-1-ethoxy-carbonylmethyl-phospholanium bromide, 1-methyl-1-benzyl-phospholanium chloride, 1-methyl-1(2-chloroethyl)-phospholanium chloride, 3,4-dichloro-1,1-dimethyl-phospholanium chloride, 1,1-dimethyl-phospholanium chloride, and 1,1-dimethyl-phospholanium methosulfate.

23. Method as claimed in claim 1 wherein said composition is applied to inhibit plant growth.

24. Method as claimed in claim 1 wherein said composition is applied to enhance plant growth.

25. Method as claimed in claim 1 wherein said composition is applied to modify plant growth.

* * * * *